(12) United States Patent
Huang et al.

(10) Patent No.: US 9,496,500 B2
(45) Date of Patent: Nov. 15, 2016

(54) ORGANIC COMPOUND AND ORGANIC ELECTROLUMINESCENT DEVICE EMPLOYING THE SAME

(71) Applicants: INDUSTRIAL TECHNOLOGY RESEARCH INSTITUTE, Chutung, Hsinchu (TW); National Tsing Hua University, Hsinchu (TW)

(72) Inventors: Heh-Lung Huang, New Taipei (TW); Cheng-An Wu, New Taipei (TW); Chien-Hong Cheng, Hsin-Chu (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 548 days.

(21) Appl. No.: 13/928,065

(22) Filed: Jun. 26, 2013

(65) Prior Publication Data
US 2014/0124752 A1    May 8, 2014

(30) Foreign Application Priority Data
Nov. 2, 2012    (TW) .............................. 101140699 A

(51) Int. Cl.
H01L 51/50    (2006.01)
H01L 51/00    (2006.01)
C09K 11/06    (2006.01)

(52) U.S. Cl.
CPC ........... H01L 51/0058 (2013.01); C09K 11/06 (2013.01); H01L 51/0054 (2013.01);
(Continued)

(58) Field of Classification Search
None
See application file for complete search history.

(56) References Cited

U.S. PATENT DOCUMENTS 4,243,673 A    1/1981 Capetola et al.
5,322,941 A    6/1994 Mees et al.
(Continued)

FOREIGN PATENT DOCUMENTS

CN    102709482 A    10/2012
JP    2011-204844    * 10/2011    ............. H01L 51/50
TW    201217309 A1    5/2012

OTHER PUBLICATIONS

Telite, New core-pyrene pi structureorganophotocatalysts usable as highly efficient photoinitiators, 2013, Beilstein Journal of Org. Chem, vol. 9, pp. 877-890.*

(Continued)

*Primary Examiner* — Gregory Clark
(74) *Attorney, Agent, or Firm* — Muncy, Geissler, Olds & Lowe PC

(57) ABSTRACT

Organic compounds and organic electroluminescence devices employing the same are provided. The organic compound has a chemical structure as represented as follows:

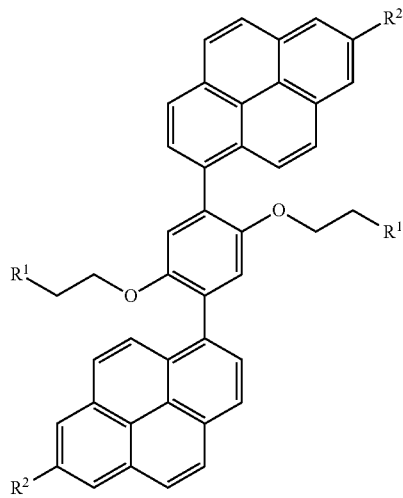

wherein, $R^1$ is independently the same or different $C_{1-6}$ alkyl, and $R^2$ is independently the same or different hydrogen, halogen, cyano, hydroxy, $C_{1-8}$ alkyl group, $C_{1-8}$ alkoxy group, $C_{5-10}$ aryl, or $C_{2-8}$ heteroaryl group.

10 Claims, 4 Drawing Sheets

(52) U.S. Cl.
CPC ... *C07C2103/50* (2013.01); *C09K 2211/1007* (2013.01); *C09K 2211/1011* (2013.01); *H01L 51/5012* (2013.01)

(56) References Cited

U.S. PATENT DOCUMENTS

| | | |
|---|---|---|
| 2003/0086964 A1 | 5/2003 | Kwon et al. |
| 2008/0095706 A1 | 4/2008 | Orser et al. |
| 2008/0274173 A1 | 11/2008 | Sill et al. |
| 2009/0169921 A1 | 7/2009 | Cheng et al. |
| 2010/0253208 A1* | 10/2010 | Cheng ............... C07D 235/02 313/504 |
| 2010/0324259 A1 | 12/2010 | Sill et al. |
| 2011/0092666 A1 | 4/2011 | Liaw |
| 2011/0233604 A1 | 9/2011 | Ikeda |
| 2012/0104364 A1 | 5/2012 | Cheng et al. |
| 2012/0168736 A1 | 7/2012 | Doi et al. |

OTHER PUBLICATIONS

Xuecheng Piao, et al., "High-efficiency blue and white organic light-emitting devices by combining fluorescent and phosphorescent blue emitters", *Organic Electronics* 13 (2012) 2412-2416.

Office Action issued on Jan. 7, 2015 for the corresponding CN patent application No. 201210551475.0.

Notice of Allowance issued on Aug. 19, 2014 for the corresponding Taiwanese application No. 101140699.

Wu et al., "The Photophysical Properties of Dipyrenylbenzenes and Their Application as Exceedingly Efficient Blue Emitters for Electroluminescent Devices," Adv. Funct. Mater., vol. 18, pp. 67-75 (2008).

Cho et al., "Highly efficient and stable deep-blue emitting anthracene-derived molecular glass for versatile types of non-doped OLED applications," J. Mater. Chem., vol. 22, pp. 123-129 (2012).

Huang et al., "Solution-processable 1,3,5-tri(9-anthracene)-benzene cored propeller-shaped materials with high $T_g$ for blue organic light-emitting diodes," Organic Electronics, vol. 12, pp. 1716-1723 (2011).

You et al., "All-solution-processed blue small molecular organic light-emitting diodes with multilayer device structure," Organic Electronics, vol. 10, pp. 1610-1614 (2009).

Yang et al., "Highly efficient greenish blue-emitting organic diodes based on pyrene derivatives," J. of Luminescence, vol. 124, pp. 93-98 (2007).

* cited by examiner

ORGANIC COMPOUND AND ORGANIC ELECTROLUMINESCENT DEVICE EMPLOYING THE SAME

CROSS REFERENCE TO RELATED APPLICATIONS

This application is based upon and claims the benefit of priority from the prior Taiwan Patent Application No. 101140699, filed on Nov. 2, 2012, the entire contents of which are incorporated herein by reference.

TECHNICAL FIELD

The disclosure relates to an organic compound and an organic electroluminescent device employing the same.

BACKGROUND

Recently, with the development and wide application of electronic products, such as mobile phones, PDAs, and notebook computers, there have been increasing demand for flat display elements which consume less electric power and occupy less space. Organic electroluminescent devices are self-emitting and highly luminous, with wide viewing angles, fast response speeds, and simple fabrication methods, making them an industry display of choice.

Generally, an organic electroluminescent device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and the hole results in light emission.

An OLED is typically categorized into a micro-molecular and high-molecular OLED according to the substrate type thereof. A micro-molecular substrate OLED is generally fabricated by way of vacuum evaporation, such that the micro-molecular materials have a good film forming quality. However, 95% of the organic electroluminescent materials are deposited on the chamber wall of the manufacturing equipment used to manufacture the OLED, such that only 5% of the organic electroluminescent materials are coated on a substrate after the manufacturing process is completed.

A wet process (such as spin coating or blade coating) has been provided to fabricate micro-molecular OLEDs to improve the utilization ratio of organic electroluminescent materials Therefore, it is necessary to develop novel organic compounds suitable for use in a wet process to fabricate phosphorescent OLEDs to solve the above problems.

SUMMARY

An exemplary embodiment of an organic compound has a Formula (I), of:

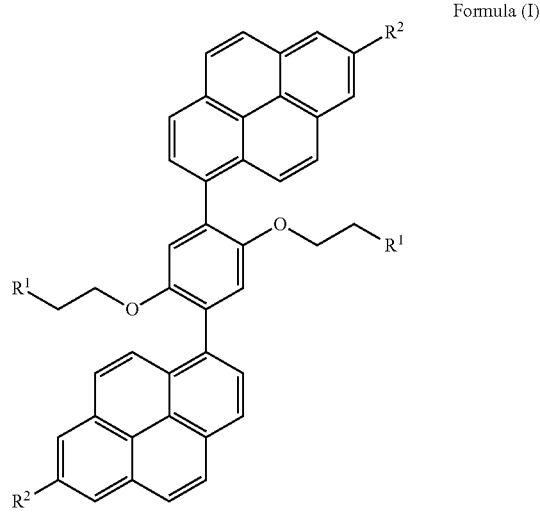

Formula (I)

wherein, $R^1$ is independently the same or different $C_{1-6}$ alkyl, and $R^2$ is independently the same or different hydrogen, halogen, cyano, hydroxy, $C_{1-8}$ alkyl, $C_{1-8}$ alkoxy group, $C_{5-10}$ aryl group, or $C_{2-8}$ heteroaryl group.

In another exemplary embodiment of the disclosure, an organic electroluminescent device is provided. The device includes a pair of electrodes and an electroluminescent element disposed between the pair of electrodes, wherein the electroluminescent element includes the aforementioned organic compound.

Yet another exemplary embodiment of the disclosure provides an organic electroluminescent device including an emission layer which includes a host material and a dopant. Particularly, the host material includes the aforementioned organic compound.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
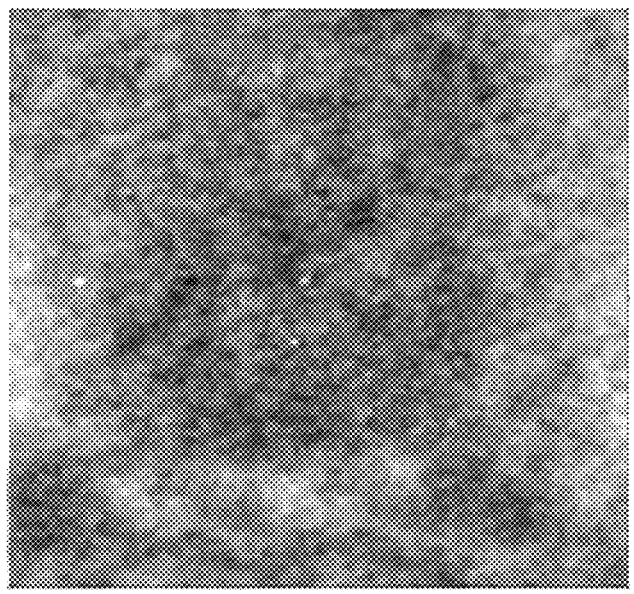
FIGS. 1-5 are topographic AFM (atomic Force Microscopy) images of the PO—$C_3$ film, the PO—$C_6$ film, the TBPO—$C_3$ film, the TBPO—$C_6$ film, and the DOPPP film.
Figure 2:
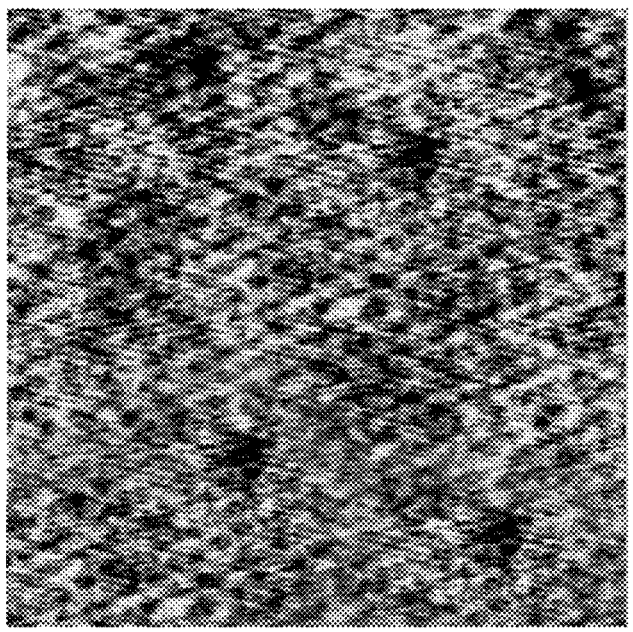
Figure 3:
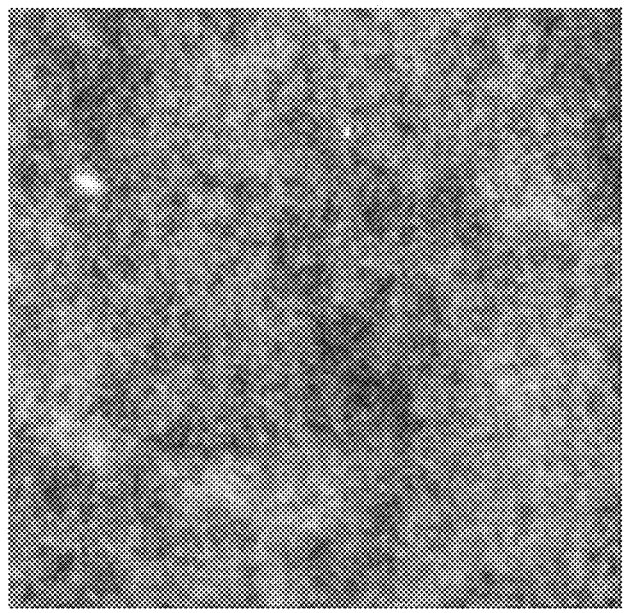
Figure 4:
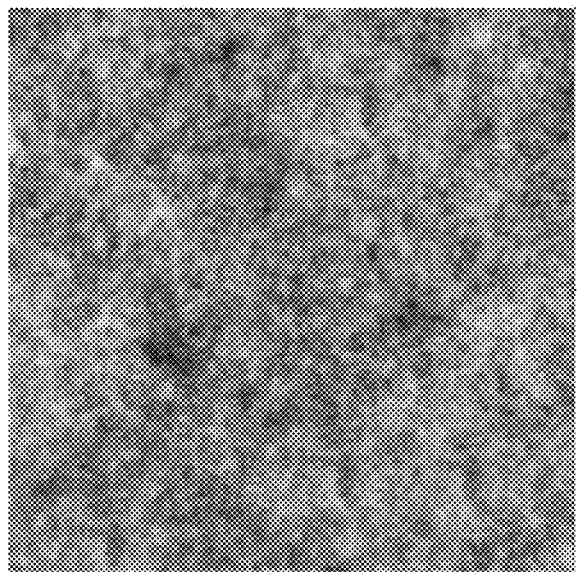
Figure 5:
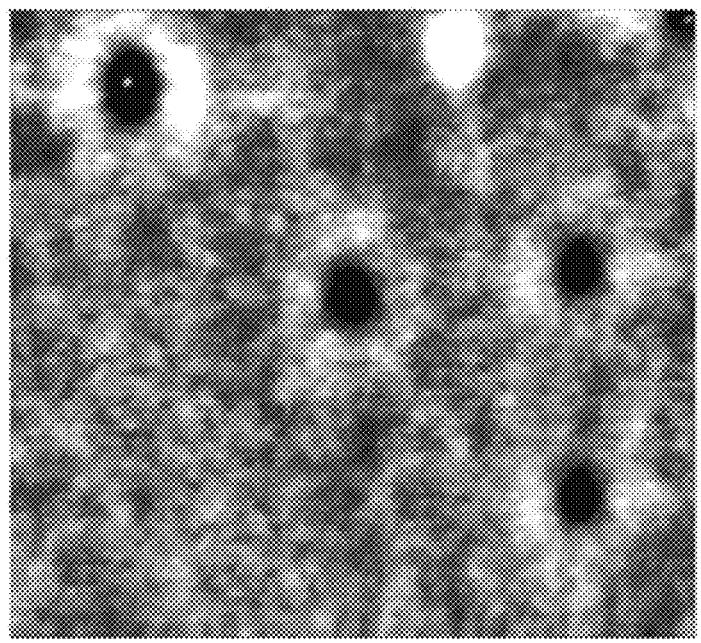

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Organic Compounds

The disclosure provides an organic compound having a structure represented by Formula (I)

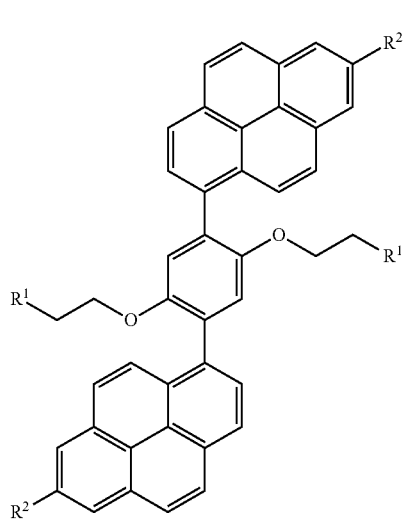

Formula (I)

wherein, $R^1$ is independently the same or different $C_{1-6}$ alkyl, and $R^2$ is independently the same or different hydrogen, halogen, cyano, hydroxy, $C_{1-8}$ alkyl, $C_{1-8}$ alkoxy, $C_{5-10}$ aryl, or $C_{2-8}$ heteroaryl According to an embodiment of the disclosure, $R^1$ can be a $C_{1-6}$ alkyl group. For example, $R^1$ is independently selected from a methyl group, ethyl group, propyl group, isopropyl group, butyl group, tert-butyl group, pentyl group, or hexyl group.

Further, $R^2$ can be independently selected from hydrogen, fluorine, chlorine, bromine, cyano, a methyl group, ethyl group, propyl group, isopropyl group, butyl group, tert-butyl group, pentyl group, hexyl group methoxy group, ethoxy group, propoxy group, isopropoxy group, butoxy group, isobutoxy group, phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

According to other embodiments of the disclosure, the organic compound of the disclosure can have a structure represented by Formula (II), or Formula (III):

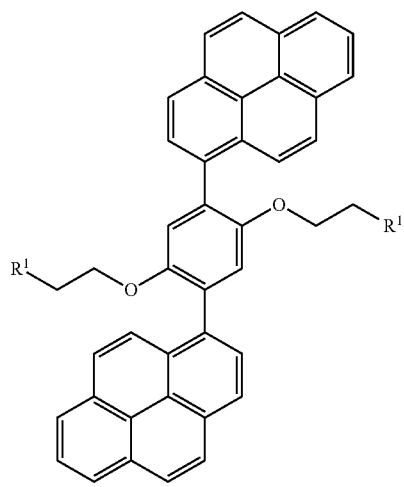

Formula (II)

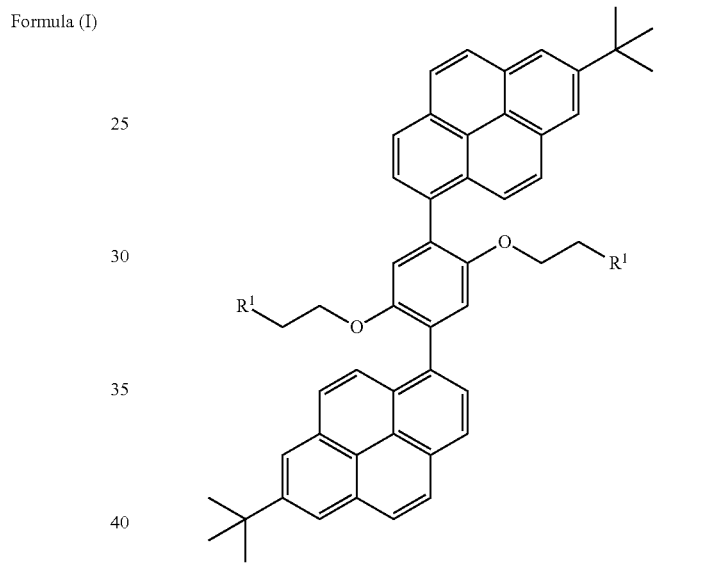

Formula (III)

wherein, $R^1$ is independently the same or different $C_{1-6}$ alkyl. Due to the high solubility of the organic compound having a structure represented by the Formula (I), the film formed by coating a solution including the organic compound via a wet process (such as spin-coating or blade-coating) exhibits superior flatness (i.e. low surface roughness).

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

The organic compounds according to the Formula (I) of the disclosure include the following compounds shown in Table 1. In addition, the contraction thereof are also named and shown in Table 1.

TABLE 1

| Example | Structure | Contraction |
|---------|-----------|-------------|
| 1 | 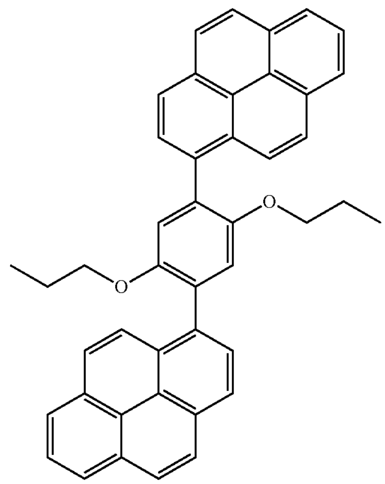 [SMILES: CCCOc1cc(-c2ccc3ccc4cccc5ccc2c3c45)c(OCCC)cc1-c1ccc2ccc3cccc4ccc1c2c34] | PO—C$_3$ |
| 2 | 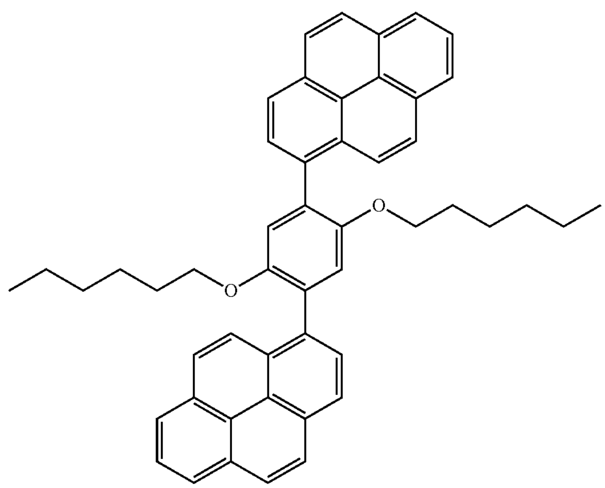 [SMILES: CCCCCCOc1cc(-c2ccc3ccc4cccc5ccc2c3c45)c(OCCCCCC)cc1-c1ccc2ccc3cccc4ccc1c2c34] | PO—C$_6$ |
| 3 | 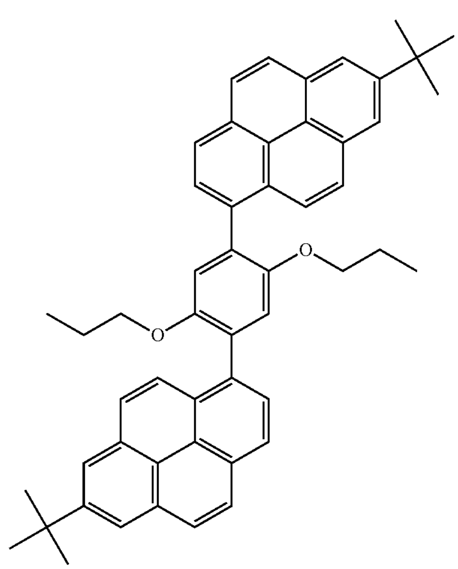 [SMILES: CCCOc1cc(-c2ccc3ccc4cc(C(C)(C)C)cc5ccc2c3c45)c(OCCC)cc1-c1ccc2ccc3cc(C(C)(C)C)cc4ccc1c2c34] | TBPO—C$_3$ |

TABLE 1-continued

| Example | Structure | Contraction |
|---------|-----------|-------------|
| 4 | 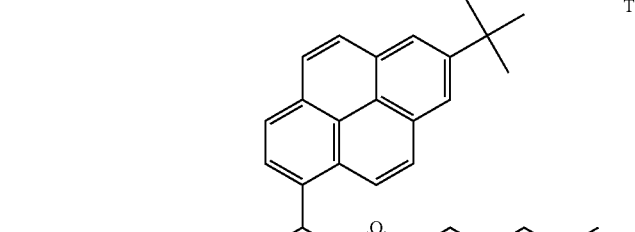 | TBPO—C$_6$ |

In order to clearly illustrate the method for preparing organic compounds according to the Formula (I), the preparation of the compounds disclosed in Examples 1-4 are described in detail as below.

Example 1

Preparation of the Compound PO—C$_3$ 5 g (18.86 mmol) of a compound (1) (2,5-dibromo-1,4-benzenediol) was added into a 250 mL reaction bottle and dissolved in 100 mL of ethanol. Next, 2.1 g (37.73 mmol) of KOH and 4.6 g (37.73 mmol) of propyl bromide were added the reaction bottle. After heating to reflux for 8 hrs, a compound (2) was obtained with a yield of 85%. The synthesis pathway of the reaction was as follows:

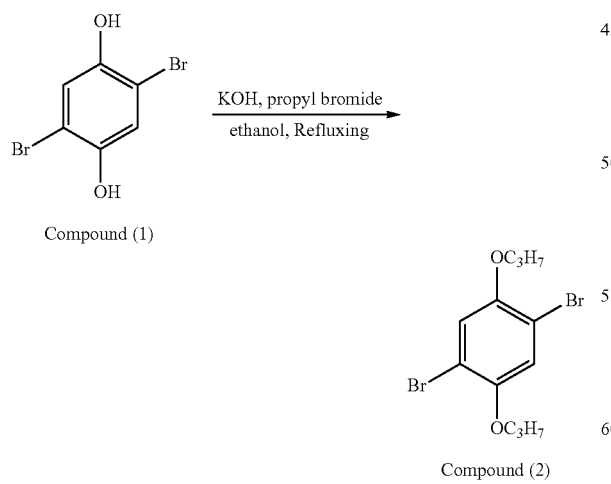

Next, 2 g (5.72 mmol) of the compound (2), 11.46 g (2.82 mmol) of a compound (3), 0.3 g of Pd(PPh$_3$)$_4$, and 4.4 g of potassium carbonate were added into a 250 mL reaction bottle and dissolved into 50 mL toluene and 16 mL DI water. The mixture was heated to reflux for 12 hrs. After cooling to room temperature, the result was subjected to a purification process (twice sublimation processes), obtaining a compound PO—C$_3$. The synthesis pathway of the reaction was as follows:

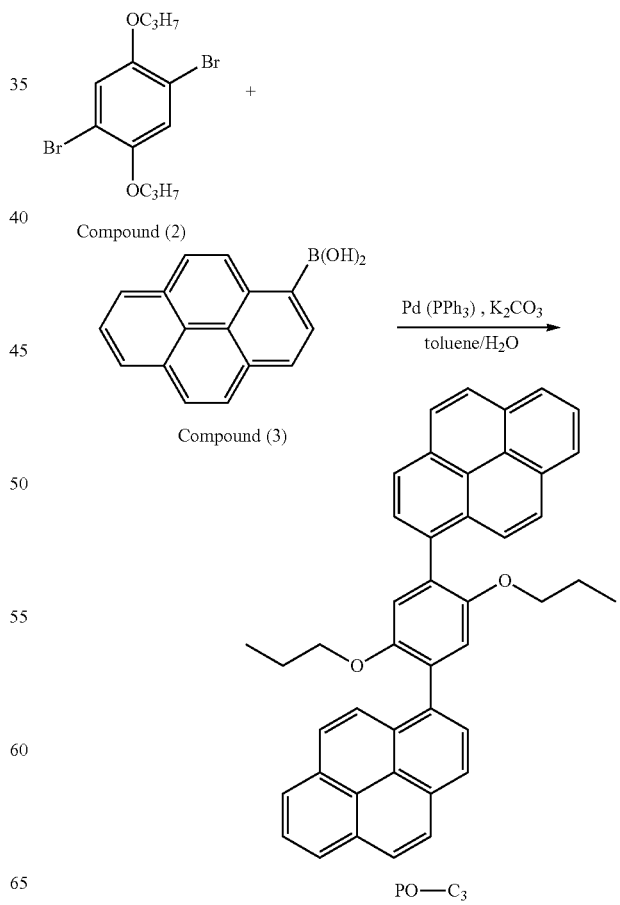

The physical measurements of the compound PO—C$_3$ are listed below:

$^1$H-NMR (400 MHz, CDCl$_3$, δ): 8.31-8.03 (m, 18H), 7.21 (s, 2H), 3.84-3.82 (t, 8 Hz, 4H), 1.44-1.39 (m, 4H), 0.60-0.56 (m, 6H).

$^{13}$C-NMR (100 MHz, CDCl$_3$, δ): 150.78, 130.57, 129.32, 128.82, 128.28, 127.60, 127.50, 127.27, 127.07, 127.00, 126.30, 126.09, 125.86, 125.25, 124.95, 124.87, 124.84, 124.52, 124.41, 117.87, 71.18, 22.49, 10.33.

High resolution mass spectrometer (HRMS EI) Calcd for C$_{44}$H$_{34}$O$_2$ (M+): 594.2559. Found: 594.2567.

Elemental analysis: C, 88.86; H, 5.76. Found: C, 88.63; H, 5.69.

Example 2

Preparation of the Compound PO—C$_6$ 5 g (18.86 mmol) of the compound (1) (2,5-Dibromo-1,4-benzenediol) was added into a 250 mL reaction bottle and dissolved in 100 mL of ethanol. Next, 2.1 g (37.73 mmol) of KOH and 6.2 g (37.73 mmol) of hexyl bromide were added into the reaction bottle. After heating to reflux for 8 hrs, a compound (4) was obtained with a yield of 80%. The synthesis pathway of the reaction was as follows:

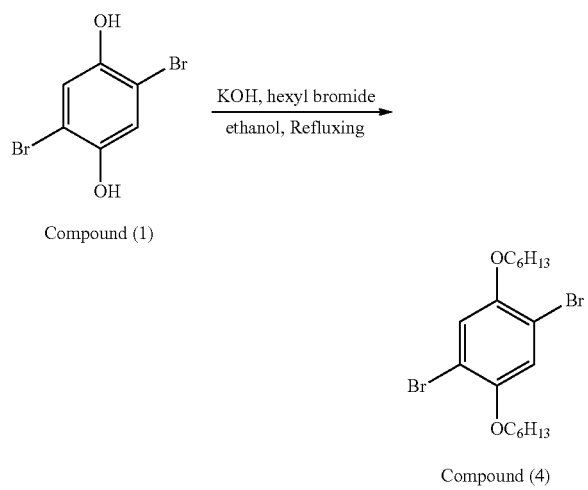

Next, 2.0 g (4.60 mmol) of the compound (4), 2.27 g (9.22 mmol) of the compound (3), 0.24 g of Pd(PPh$_3$)$_4$, and 4.4 g of potassium carbonate were added into a 250 mL reaction bottle and dissolved into 50 mL toluene and 16 mL DI water. The mixture was heated to reflux for 12 hrs. After cooling to room temperature, the result was subjected to a purification process (twice sublimation processes), obtaining a compound PO—C$_6$. The synthesis pathway of the reaction was as follows:

The physical measurements of the compound PO—C$_6$ are listed below:

$^1$H-NMR (400 MHz, CDCl$_3$, δ): 8.29-8.00 (m, 18H), 7.20 (s, 2H), 3.84-3.82 (t, J=8 Hz, 4H), 1.36-1.33 (m, 4H), 0.88-0.87 (m, 12H), 0.54-0.51 (m, 6H).

$^{13}$C-NMR (100 MHz, CDCl$_3$, δ): 150.91, 134.16, 130.76, 130.74, 130.66, 129.35, 129.32, 128.28, 127.47, 127.37, 127.27, 127.10, 127.03, 126.29, 125.85, 124.96, 124.85, 124.82, 124.41, 118.02, 117.99, 69.76, 31.16, 29.10, 25.39, 22.24, 13.65.

High resolution mass spectrometer (HRMS EI) Calcd for C$_{50}$H$_{46}$O$_2$ (M+): 678.3498. Found: 678.3498.

Elemental analysis: C, 88.46; H, 6.83. Found: C, 88.59; H, 6.69.

Example 3

Preparation of the Compound TBPO—C$_3$ 2 g (5.72 mmol) of the compound (2), 3.46 g (11.46 mmol) of a compound (5), 0.3 g of Pd(PPh$_3$)$_4$, and 4.4 g of potassium carbonate was added into a 250 mL reaction bottle and dissolved into 50 mL toluene and 16 mL DI water. The mixture was heated to reflux for 12 hrs. After cooling to room temperature, the result was subjected to a purification process (twice sublimation processes), obtaining a compound TBPO—C$_3$. The synthesis pathway of the reaction was as follows:

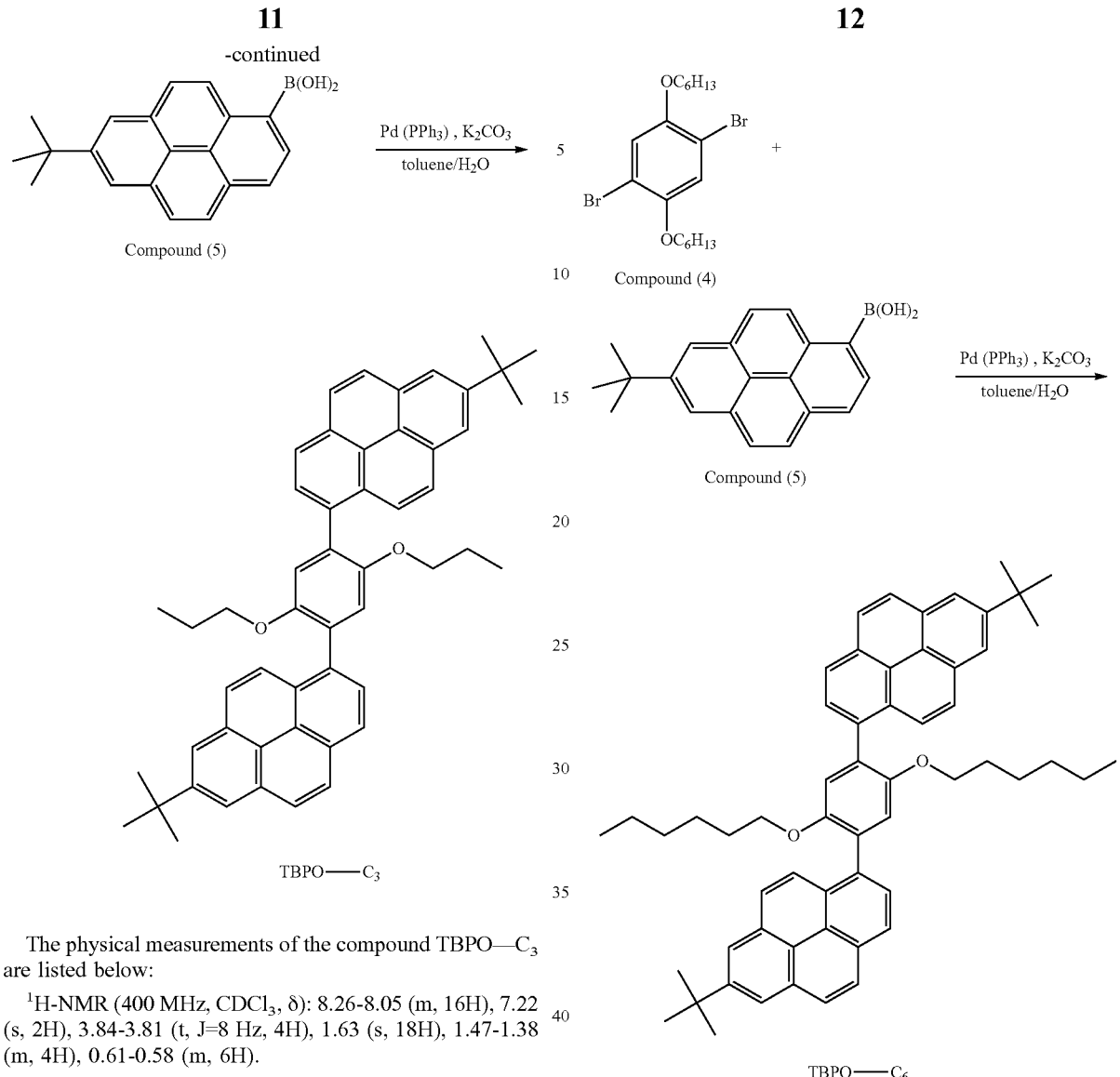

The physical measurements of the compound TBPO—C$_3$ are listed below:

$^1$H-NMR (400 MHz, CDCl$_3$, δ): 8.26-8.05 (m, 16H), 7.22 (s, 2H), 3.84-3.81 (t, J=8 Hz, 4H), 1.63 (s, 18H), 1.47-1.38 (m, 4H), 0.61-0.58 (m, 6H).

$^{13}$C-NMR (100 MHz, CDCl$_3$, δ): 150.80, 148.96, 134.29, 131.26, 130.94, 130.69, 130.45, 129.14, 127.95, 127.44, 127.35, 127.23, 127.18, 126.19, 124.75, 124.19, 123.12, 122.24, 122.21, 117.98, 71.24, 35.22, 31.95, 22.50, 10.34.

High resolution mass spectrometer (HRMS EI) Calcd for C$_{52}$H$_{50}$O$_2$ (M+): 706.3811. Found: 706.3820.

Elemental analysis: C, 88.34; H, 7.13. Found: C, 88.20; H, 7.05.

Example 4

Preparation of the compound TBPO—C$_6$

Next, 2.0 g (4.6 mmol) of the compound (4), 2.3 g (9.22 mmol) of the compound (5), 0.24 g of Pd(PPh$_3$)$_4$, and 4.4 g of potassium carbonate were added into a 250 mL reaction bottle and dissolved into 50 mL toluene and 16 mL DI water. The mixture was heated to reflux for 12 hrs. After cooling to room temperature, the result was subjected to a purification process (twice sublimation processes), obtaining a compound. The synthesis pathway of the reaction was as follows:

The physical measurements of the compound TBPO—C$_6$ are listed below:

$^1$H-NMR (400 MHz, CDCl$_3$, δ): 8.28-8.04 (m, 16H), 7.24 (s, 2H), 3.84-3.81 (t, J=8 Hz, 4H), 1.63 (s, 18H), 1.39-1.35 (m, 4H), 0.91-0.90 (m, 12H), 0.59-0.55 (m, 6H).

$^{13}$C-NMR (100 MHz, CDCl$_3$, δ): 150.93, 148.96, 134.26, 131.26, 130.96, 130.84, 130.47, 129.17, 127.91, 127.44, 127.32, 127.27, 127.22, 126.22, 124.75, 124.20, 123.13, 122.18, 122.11, 118.60, 69.82, 35.22, 31.95, 31.22, 29.16, 25.46, 22.27, 13.69.

High resolution mass spectrometer (HRMS EI) Calcd for C$_{58}$H$_{62}$O$_2$ (M+): 790.4750. Found: 790.4746.

Elemental analysis: C, 88.06; H, 7.90. Found: C, 87.75; H, 7.92.

Properties of the Organic Compounds

The melting point (T$_m$), decomposition temperature (T$_d$), HOMO (highest occupied molecular orbital), and LUMO (lowest unoccupied molecular orbital) energy gap of the compounds PO—C$_3$, PO—C$_6$, TBPO—C$_3$, and TBPO—C$_6$ were measured and are shown in Table 2.

TABLE 2

| compound | PO—$C_3$ | PO—$C_6$ | TBPO—$C_3$ | TBPO—$C_6$ |
|---|---|---|---|---|
| $T_m$ | 257° C. | 170° C. | — | 218° C. |
| $T_d$ | 381° C. | 384° C. | 395° C. | 365° C. |
| LUMO | 2.68 | 2.71 | 2.38 | 2.47 |
| HOMO | 5.67 | 5.75 | 5.42 | 5.50 |

As shown in Table 2, since the decomposition temperature ($T_d$) of the compounds PO—$C_3$, PO—$C_6$, TBPO—$C_3$, and TBPO—$C_6$ of the disclosure were all higher than 350□, the compounds having the Formula (I) of the disclosure exhibited higher thermal stability. Further, the compounds PO—$C_3$, PO—$C_6$, TBPO—$C_3$, and TBPO—$C_6$ also had suitable LUMO and HOMO energy gaps, thereby being able to substantially enhance the electroluminescent efficiency of an organic electroluminescence device employing the same.

Film-Forming Ability Test 0.26 g of the compound PO—$C_3$, PO—$C_6$, TBPO—$C_3$, and TBPO—$C_6$, and a compound DOPPP (1,1'-(dimethoxy-1,4'-phenylene)dipyrene, having a structure represented by

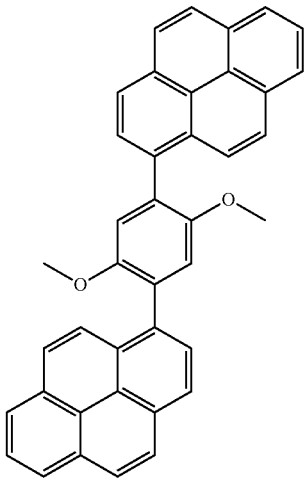

were dissolved in 2.97 g of toluene respectively. After stirring, the solutions were respectively coated on a glass substrate by spin-coating (at 700-2000 rpm). After baking, a PO—$C_3$ film, a PO—$C_6$ film, a TBPO—$C_3$ film, a TBPO—$C_6$ film, and a DOPPP film (with a thickness of 30-65 nm) were obtained.

Next, the RMS (root mean square) roughness of the PO—$C_3$ film, the PO—$C_6$ film, the TBPO—$C_3$ film, the TBPO—$C_6$ film, and the DOPPP film were measured respectively. The results showed that the RMS roughness of the DOPPP film was larger than 0.56 nm. The RMS roughness of the PO—$C_3$ and PO—$C_6$ films were both less than 0.50 nm (such as 0.44 nm). In comparison with the DOPPP film, the RMS roughness of the PO—$C_3$ and PO—$C_6$ films were lower by 21%. On the other hands, the RMS roughness of the TBPO—$C_3$ and TBPO—$C_6$ films were both about 0.35 nm. In comparison with the DOPPP film, the RMS roughness of the TBPO—$C_3$ and TBPO—$C_6$ films were lower by 37%. Accordingly, due to the superior solubility of the compounds of the disclosure, the films made from the compounds of the disclosure exhibited high film-forming ability and had low surface roughness. Therefore, an organic electroluminescence device employing the films made from the compounds of the disclosure can have improved photoelectric properties and a low current leakage.

FIGS. 1-5 are topographic AFM (Atomic Force Microscopy) images of the PO—$C_3$ film, the PO—$C_6$ film, the TBPO—$C_3$ film, the TBPO—$C_6$ film, and the DOPPP film (with a feature resolution of 5×5 μm). As shown in FIGS. 1-5, the DOPPP film had inferior surface flatness, in comparison with the PO—$C_3$ film, the PO—$C_6$ film, the TBPO—$C_3$ film, and the TBPO—$C_6$ film.

Organic Electroluminescence Device

Figure 6:
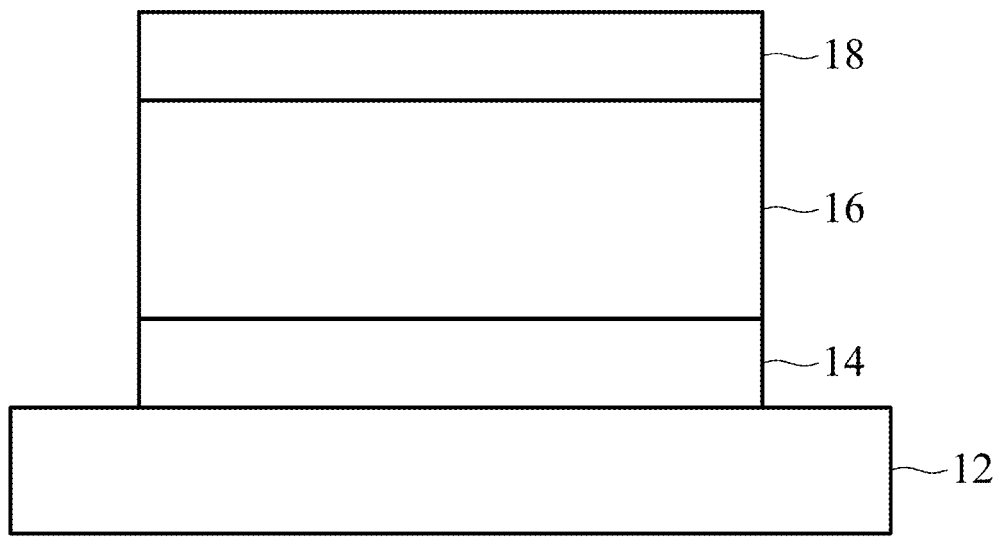
FIG. 6 shows a cross section of an organic electroluminescent device disclosed by an embodiment of the disclosure.

FIG. 6 shows an embodiment of an organic electroluminescent device 10. The electroluminescent device 100 includes a substrate 12, a bottom electrode 14, an electroluminescent element 16, and a top electrode 18, as shown in FIG. 6. The organic electroluminescent device can be top-emission, bottom-emission, or dual-emission devices.

The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, al least one of the bottom and top electrodes 14 and 18 is transparent.

The electroluminescent element 16 at least includes an emission layer, and can further include a hole injection layer, a hole transport layer, an electron transport layer, and an electron injection layer. In an embodiment of the disclosure, at least one layer of the electroluminescent element 16 includes the aforementioned organic compound.

According to another embodiment of the disclosure, the emission layer of the electroluminescent element can include a host material and a dopant, wherein the host material can include the aforementioned organic compounds. The dose of the dopant is not limited and can be optionally modified by a person of ordinary skill in the field.

The method for forming the emission layer including the organic compound having a structure represented by the Formula (I) can be a dry process (such as a thermal vacuum evaporation, a physical vapor deposition, or a chemical vapor deposition) or a wet process (a spin coating, or an ink-jet printing wet process). Due to high solubility, the organic compounds having the structure represented by the Formula (I) are suitable for being formed into a film via a wet process.

In order to clearly disclose the organic electroluminescent devices of the disclosure, the following examples (using the aforementioned compounds as host materials with/without a dopant) are intended to illustrate the disclosure more fully without limiting their scope, since numerous modifications and variations will be apparent to those skilled in this art.

Example 5

Organic Electroluminescence Device (1)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)-ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, PO—$C_3$ was coated onto the PEDOT:PSS film by a spin-coating process (with a rotation rate of 700 rpm for 30 sec) and dried under vacuum for 40 min, obtaining a PO—$C_3$ film. Next, TPBI (1,3,5-tris (phenyl-2-benzimidazolyl)-benzene, with a thickness of 40 nm), LiF (with a thickness of 1 nm), and Al (with a thickness of 100 nm) were subsequently formed on the PO—$C_3$ film at $1\times10^{-6}$ Pa, to obtain the electroluminescent device (1). The materials and layers formed therefrom are described in the following: ITO(120 nm)/PEDOT:PSS/PO—$C_3$(700 rpm for 30 min)/TPBI(40 nm)/LiF(1 nm)/Al(100 nm)

Next, the properties of the electroluminescent device (1) were measured by a PR650 (purchased from Photo Research Inc.) and a Minolta TS110. The results are shown in Table 3

Example 6

Organic Electroluminescence Device (2)

Example 6 was performed in the same manner as in Example 5 except that the PO—$C_3$ film was formed by the spin-coating process with a rotation rate of 1000 rpm for 30 sec, to obtain the electroluminescent device (2). The materials and layers formed therefrom are described in the following: ITO(120 nm)/PEDOT:PSS/PO—$C_3$(1000 rpm for 30 min)/TPBI(40 nm)/LiF(1 nm)/Al(100 nm)

Next, the properties of the electroluminescent device (2) were measured by a PR650 (purchased from Photo Research Inc.) and a Minolta TS110. The results are shown in Table 3

Example 7

Organic Electroluminescence Device (3)

Example 7 was performed in the same manner as in Example 5 except that the PO—$C_3$ film was formed by the spin-coating process with a rotation rate of 1500 rpm for 30 sec, to obtain the electroluminescent device (3). The materials and layers formed therefrom are described in the following: ITO(120 nm)/PEDOT:PSS/PO—$C_3$(1500 rpm for 30 min)/TPBI(40 nm)/LiF(1 nm)/Al(100 nm)

Next, the properties of the electroluminescent device (3) were measured by a PR650 (purchased from Photo Research Inc.) and a Minolta TS110. The results are shown in Table 3

Example 8

Organic Electroluminescence Device (4)

Example 8 was performed in the same manner as in Example 5 except that the PO—$C_3$ film was formed by the spin-coating process with a rotation rate of 2000 rpm for 30 sec, to obtain the electroluminescent device (4). The materials and layers formed therefrom are described in the following: ITO(120 nm)/PEDOT:PSS/PO—$C_3$(2000 rpm for 30 min)/TPBI(40 nm)/LiF(1 nm)/Al(100 nm)

Next, the properties of the electroluminescent device (4) were measured by a PR650 (purchased from Photo Research Inc.) and a Minolta TS 110. The results are shown in Table 3.

TABLE 3

| | organic electroluminescence device (1) | organic electroluminescence device (2) | organic electroluminescence device (3) | organic electroluminescence device (4) |
|---|---|---|---|---|
| driving voltage (V) | 3.07 | 3.08 | 3.03 | 3.02 |
| current efficiency (cd/A) (measured at a brightness of 1000 Cd/m2) | 6.59 | 6.14 | 6.68 | 4.44 |
| power efficiency (lm/W) (measured at a brightness of 1000 Cd/m2) | 4.42 | 4.06 | 4.58 | 3.11 |
| CIE (X, Y) (measured at a voltage of 8 V) | (0.17, 0.29) | (0.17, 0.30) | (0.17, 0.32) | (0.16, 0.24) |

Example 9

Organic Electroluminescence Device (5)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)-ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, PO—$C_6$ was coated onto the PEDOT:PSS film by a spin-coating process (with a rotation rate of 700 rpm for 30 sec) and dried under vacuum for 40 min, obtaining a PO—$C_3$ film. Next, TPBI (1,3,5-tris (phenyl-2-benzimidazolyl)-benzene, with a thickness of 40 nm), LiF (with a thickness of 1 nm), and Al (with a thickness of 100 nm) were subsequently formed on the PO—$C_3$ film at $1\times10^{-6}$ Pa, to obtain the electroluminescent device (5). The materials and layers formed therefrom are described in the following: ITO(120 nm)/PEDOT:PSS/PO—$C_6$(700 rpm for 30 min)/TPBI(40 nm)/LiF(1 nm)/Al(100 nm)

Next, the properties of the electroluminescent device (5) were measured by a PR650 (purchased from Photo Research Inc.) and a Minolta TS110. The results are shown in Table 4

Example 10

Organic Electroluminescence Device (6)

Example 10 was performed in the same manner as in Example 9 except that the PO—$C_6$ film was formed by the spin-coating process with a rotation rate of 1000 rpm for 30 sec, to obtain the electroluminescent device (6). The materials and layers formed therefrom are described in the following: ITO(120 nm)/PEDOT:PSS/PO—$C_6$(1000 rpm for 30 min)/TPBI(40 nm)/LiF(1 nm)/Al(100 nm)

Next, the properties of the electroluminescent device (6) were measured by a PR650 (purchased from Photo Research Inc.) and a Minolta TS110. The results are shown in Table 4

Example 11

Organic Electroluminescence Device (7)

Example 11 was performed in the same manner as in Example 9 except that the PO—$C_6$ film was formed by the spin-coating process with a rotation rate of 1500 rpm for 30 sec, to obtain the electroluminescent device (7). The materials and layers formed therefrom are described in the following: ITO(120 nm)/PEDOT:PSS/PO—$C_6$(1500 rpm for 30 min)/TPBI(40 nm)/LiF(1 nm)/Al(100 nm)

Next, the properties of the electroluminescent device (7) were measured by a PR650 (purchased from Photo Research Inc.) and a Minolta TS110. The results are shown in Table 4

Example 12

Organic Electroluminescence Device (8)

Example 12 was performed in the same manner as in Example 9 except that the PO—$C_6$ film was formed by the spin-coating process with a rotation rate of 2000 rpm for 30 sec, to obtain the electroluminescent device (8). The materials and layers formed therefrom are described in the following: ITO(120 nm)/PEDOT:PSS/PO—$C_6$(2000 rpm for 30 min)/TPBI(40 nm)/LiF(1 nm)/Al(100 nm)

Next, the properties of the electroluminescent device (8) were measured by a PR650 (purchased from Photo Research Inc.) and a Minolta TS110. The results are shown in Table 4.

TABLE 4

|  | organic electroluminescence device (5) | organic electroluminescence device (6) | organic electroluminescence device (7) | organic electroluminescence device (8) |
|---|---|---|---|---|
| driving voltage (V) | 3.0 | 3.4 | 4.2 | 3.0 |
| current efficiency (cd/A) (measured at a brightness of 1000 Cd/m2) | 6.22 | 5.57 | 5.19 | 4.75 |
| power efficiency (lm/W) (measured at a brightness of 1000 Cd/m2) | 4.34 | 3.94 | 3.86 | 3.49 |
| CIE (X, Y) (measured at a voltage of 8 V) | (0.18, 0.39) | (0.17, 034) | (0.16, 0.34) | (0.17, 0.30) |

Example 13

Organic Electroluminescence Device (9)

Example 13 was performed in the same manner as in Example 9 except that the thickness of TBPI was increased from 40 nm to 60 nm, to obtain the electroluminescent device (9). The materials and layers formed therefrom are described in the following: ITO(120 nm)/PEDOT:PSS/PO—$C_6$(700 rpm for 30 min)/TPBI(60 nm)/LiF(1 nm)/Al (100 nm)

Next, the properties of the electroluminescent device (9) were measured by a PR650 (purchased from Photo Research Inc.) and a Minolta TS110. The results are shown in Table 5

Example 14

Organic Electroluminescence Device (10)

Example 14 was performed in the same manner as in Example 9 except that the thickness of TBPI was increased from 40 nm to 50 nm, to obtain the electroluminescent device (10). The materials and layers formed therefrom are described in the following: ITO(120 nm)/PEDOT:PSS/PO—$C_6$(700 rpm for 30 min)/TPBI(50 nm)/LiF(1 nm)/Al (100 nm)

Next, the properties of the electroluminescent device (10) were measured by a PR650 (purchased from Photo Research Inc.) and a Minolta TS110. The results are shown in Table 5

Example 15

Organic Electroluminescence Device (11)

Example 15 was performed in the same manner as in Example 9 except for the substitution of BCP (2,9-dimethyl-4,7diphenyl-1,10-phenanthroline, with a thickness of 40 nm) for TPBI, to obtain the electroluminescent device (11). The materials and layers formed therefrom are described in the following: ITO(120 nm)/PEDOT:PSS/PO—$C_6$(700 rpm for 30 min)/BCP(40 nm)/LiF(1 nm)/Al(100 nm)

Next, the properties of the electroluminescent device (11) were measured by a PR650 (purchased from Photo Research Inc.) and a Minolta TS110. The results are shown in Table 5.

TABLE 5

|  | organic electroluminescence device (9) | organic electroluminescence device (10) | organic electroluminescence device (11) |
|---|---|---|---|
| driving voltage (V) | 3.55 | 3.13 | 3.85 |
| current efficiency (cd/A) (measured at a brightness of 1000 Cd/m2) | 7.53 | 10.6 | 4.61 |
| power efficiency(lm/W) (measured at a brightness of 1000 Cd/m2) | 4.5 | 7.38 | 2.32 |
| CIE (X, Y) (measured at a voltage of 8 V) | (0.20, 0.37) | (0.20, 0.45) | (0.19, 0.46) |

Example 16

Organic Electroluminescence Device (12)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)- ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, a mixture of PO—$C_3$ and BCzVBi (having a structure represented by

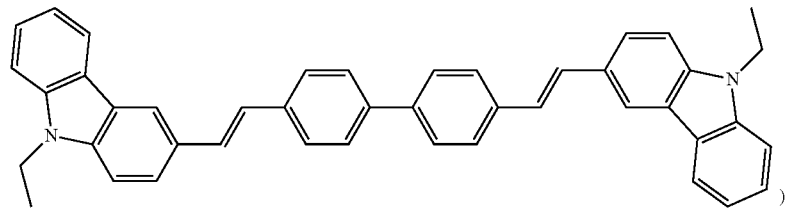

(the ratio between PO—$C_3$ and BCzVBi was 100:3) was coated onto the PEDOT:PSS film by a spin-coating process (with a rotation rate of 700 rpm for 30 sec) and dried under vacuum for 40 min, obtaining a PO—$C_3$/BCzVBi film. Next, TPBI (1,3,5-tris(phenyl-2-benzimidazolyl)-benzene, with a thickness of 40 nm), LiF (with a thickness of 1 nm), and Al (with a thickness of 100 nm) were subsequently formed on the PO—$C_3$/BCzVBi film at $1\times10^{-6}$ Pa, to obtain the electroluminescent device (12). The materials and layers formed therefrom are described in the following: ITO(120 nm)/PEDOT:PSS/PO—$C_3$/BCzVBi (700 rpm for 30 min, BCzVBi 3%)/TPBI(40 nm)/LiF(1 nm)/Al(100 nm)

Next, the properties of the electroluminescent device (12) were measured by a PR650 (purchased from Photo Research Inc.) and a Minolta TS110. The results are shown in Table 6

Example 17

Organic Electroluminescence Device (13)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)-ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, a mixture of PO—$C_3$ and BCzVBi (having a structure represented by (the ratio between PO—$C_6$ and BCzVBi was 100:3) was coated onto the PEDOT:PSS film by a spin-coating process (with a rotation rate of 700 rpm for 30 sec) and dried under vacuum for 40 min, obtaining a PO—$C_6$/BCzVBi film. Next, TPBI (1,3,5-tris(phenyl-2-benzimidazolyl)-benzene, with a thickness of 40 nm), LiF (with a thickness of 1 nm), and Al (with a thickness of 100 nm) were subsequently formed on the PO—$C_6$/BCzVBi film at $1\times10^{-6}$ Pa, to obtain the electroluminescent device (13). The materials and layers formed therefrom are described in the following: ITO(120 nm)/PEDOT:PSS/PO—$C_6$:BCzVBi (700 rpm for 30 min, BCzVBi 3%)/TPBI(40 nm)/LiF(1 nm)/Al(100 nm)

Next, the properties of the electroluminescent device (13) were measured by a PR650 (purchased from Photo Research Inc.) and a Minolta TS110. The results are shown in Table 6

Example 18

Organic Electroluminescence Device (14)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)-ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, a mixture of TBPO—$C_3$ and BCzVBi (having a structure represented by

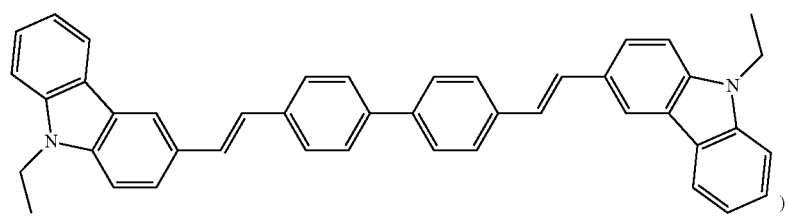 [SMILES: CCn1c2ccccc2c2cc(/C=C/c3ccc(-c4ccc(/C=C/c5ccc6c(c5)c5ccccc5n6CC)cc4)cc3)ccc21]

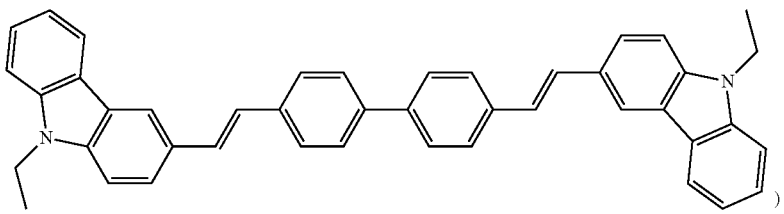 [SMILES: CCn1c2ccccc2c2cc(/C=C/c3ccc(-c4ccc(/C=C/c5ccc6c(c5)c5ccccc5n6CC)cc4)cc3)ccc21]

(the ratio between TBPO—C$_3$ and BCzVBi was 100:3) was coated onto the PEDOT:PSS film by a spin-coating process (with a rotation rate of 700 rpm for 30 sec) and dried under vacuum for 40 min, obtaining a TBPO—C$_3$/BCzVBi film. Next, TPBI (1,3,5-tris(phenyl-2-benzimidazolyl)-benzene, with a thickness of 40 nm), LiF (with a thickness of 1 nm), and Al (with a thickness of 100 nm) were subsequently formed on the TBPO—C$_3$/BCzVBi film at 1×10$^{-6}$ Pa, to obtain the electroluminescent device (14). The materials and layers formed therefrom are described in the following: ITO(120 nm)/PEDOT:PSS/TBPO—C$_3$:BCzVBi (700 rpm for 30 min, BCzVBi 3%)/TPBI(40 nm)/LiF(1 nm)/Al(100 nm)

Next, the properties of the electroluminescent device (14) were measured by a PR650 (purchased from Photo Research Inc.) and a Minolta TS110. The results are shown in Table 6

Example 19

Organic Electroluminescence Device (15)

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, PEDOT (poly(3,4)-ethylendioxythiophen):PSS(e-polystyrenesulfonate) was coated onto the ITO film by a spin coating process (with a rotation rate of 300 rpm for 5 sec and 2500 rpm for 25 sec), and baked at 100° C. for 40 min to form a PEDOT:PSS film (serving as a hole-inject layer). Next, a mixture of TBPO—C$_6$ and BCzVBi (having a structure represented by

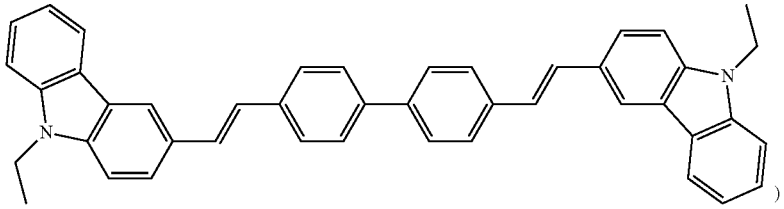 [SMILES: CCn1c2ccccc2c2cc(/C=C/c3ccc(-c4ccc(/C=C/c5ccc6c(c5)c5ccccc5n6CC)cc4)cc3)ccc21]

(the ratio between TBPO—C$_6$ and BCzVBi was 100:3) was coated onto the PEDOT:PSS film by a spin-coating process (with a rotation rate of 700 rpm for 30 sec) and dried under vacuum for 40 min, obtaining a TBPO—C$_6$/BCzVBi film. Next, TPBI (1,3,5-tris(phenyl-2-benzimidazolyl)-benzene, with a thickness of 40 nm), LiF (with a thickness of 1 nm), and Al (with a thickness of 100 nm) were subsequently formed on the TBPO—C$_6$/BCzVBi film at 1×10$^{-6}$ Pa, to obtain the electroluminescent device (15). The materials and layers formed therefrom are described in the following: ITO(120 nm)/PEDOT:PSS/TBPO—C$_6$:BCzVBi (700 rpm for 30 min, BCzVBi 3%)/TPBI(40 nm)/LiF(1 nm)/Al(100 nm)

Next, the properties of the electroluminescent device (15) were measured by a PR650 (purchased from Photo Research Inc.) and a Minolta TS110. The results are shown in Table 6.

TABLE 6

| | organic electroluminescence device (12) | organic electroluminescence device (13) | organic electroluminescence device (14) | organic electroluminescence device (15) |
|---|---|---|---|---|
| driving voltage (V) | 4.2 | 4.5 | 4.1 | 5.2 |
| current efficiency (cd/A) (measured at a brightness of 1000 Cd/m2) | 5.3 | 4.3 | 5.2 | 5.8 |
| power efficiency (lm/W) (measured at a brightness of 1000 Cd/m2) | 2.7 | 2.2 | 2.5 | 2.3 |
| CIE (X, Y) (measured at a voltage of 8 V) | (0.15, 0.18) | (0.14, 0.12) | (0.17, 0.23) | (0.18, 0.26) |

Accordingly, due to the superior solubility of the compounds having a structure of the Formula (I) of the disclosure, the films made from the aforementioned compounds can exhibit high film-forming ability and have low surface roughness. Therefore, an organic electroluminescence device employing the films made from the aforementioned compounds can have improved performances.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. An organic compound having a Formula (I), of:

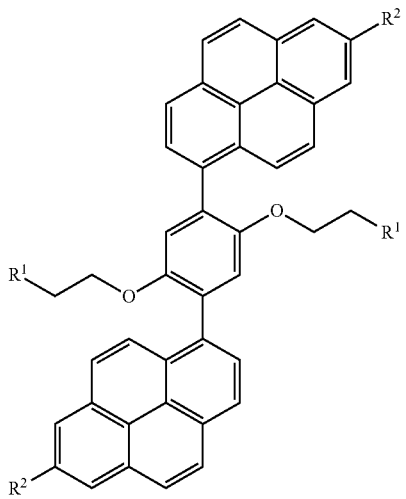

Formula (I)

wherein, $R^1$ is independently the same or different $C_{1-6}$ alkyl, and $R^2$ is independently the same or different hydrogen, halogen, cyano, hydroxy, $C_{1-8}$ alkyl group, $C_{1-8}$ alkoxy group, $C_{5-10}$ aryl, or $C_{2-8}$ heteroaryl group.

2. The organic compound as claimed in claim 1, wherein $R^1$ is independent a methyl group, ethyl group, propyl group, isopropyl group, butyl group, tert-butyl group, pentyl group, or hexyl group.

3. The organic compound as claimed in claim 1, wherein $R^2$ is independent a methyl group, ethyl group, propyl group, isopropyl group, butyl group, tert-butyl group, pentyl group, or hexyl group.

4. The organic compound as claimed in claim 1, wherein $R^2$ is independent a methoxy group, ethoxy group, propoxy group, isopropoxy group, butoxy group, isobutoxy group, pentyloxy group, or hexyloxy group.

5. The organic compound as claimed in claim 1, wherein $R^2$ is independent a phenyl group, biphenyl group, pyridyl group, furyl group naphthyl group, anthryl group, phenanthrenyl group, imidazolyl group, pyrimidinyl group, quinolinyl group, indolyl group, or thiazolyl group.

6. The organic compound as claimed in claim 1, wherein the organic compound comprises

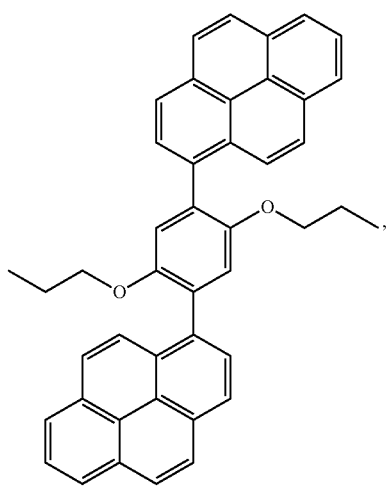

,

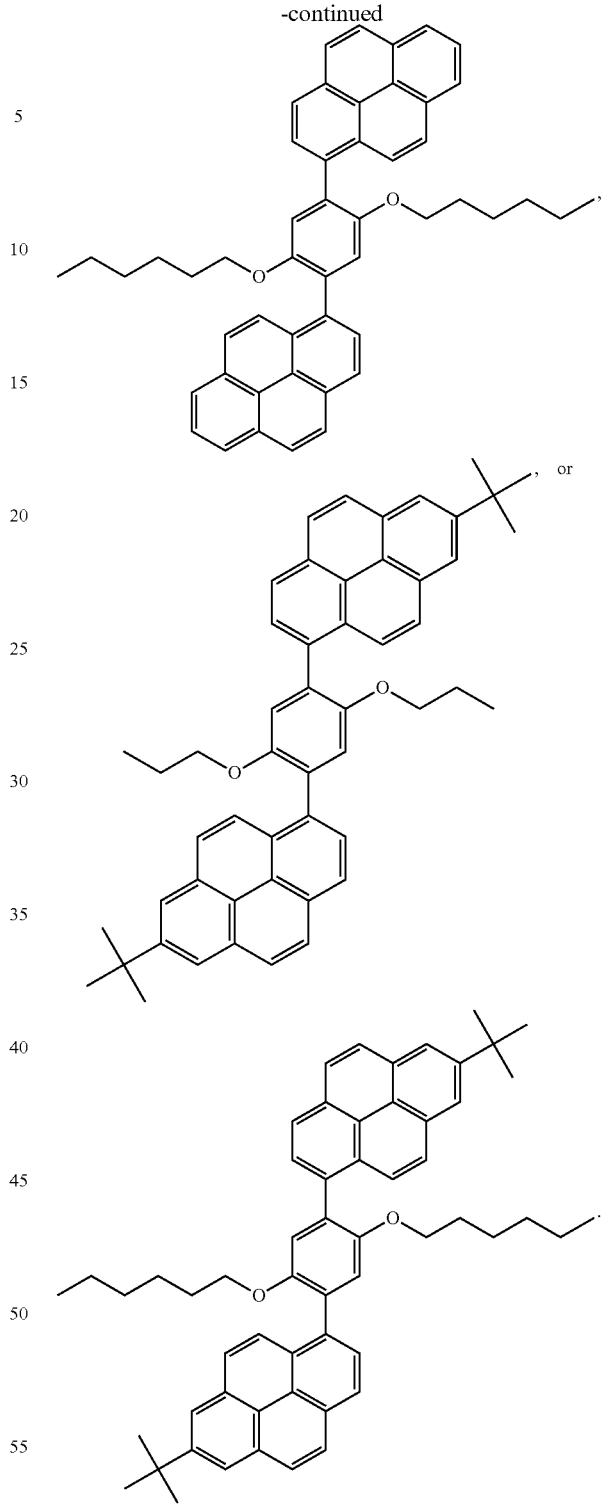

7. An organic electroluminescence device, comprising:
   a pair of electrodes; and
   an electroluminescent element, disposed between the pair of electrodes, wherein the electroluminescent element comprises the organic compound as claimed in claim 1.

8. The organic electroluminescence device as claimed in claim 7, wherein the electroluminescent element emits blue light under a bias voltage.

9. An organic electroluminescence device, comprising:
a pair of electrodes; and
an electroluminescent element disposed between the pair of electrodes, wherein the electroluminescent element comprises an emission layer and the emission layer comprises a host material and a dopant, and the host material comprises the organic compound as claimed in claim 1.

10. The organic electroluminescence device as claimed in claim 9, wherein the emission layer emits blue light under a bias voltage.

* * * * *